(12) United States Patent
Sledge (10) Patent No.: US 8,323,345 B2
(45) Date of Patent: Dec. 4, 2012

(54) ANTERIOR LUMBAR INTERBODY FUSION CAGE DEVICE AND ASSOCIATED METHOD

(75) Inventor: John B. Sledge, Marblehead, MA (US)

(73) Assignee: U.S. Spine, Inc., Salt Lake City, UT (US)

( * ) Notice: Subject to any disclaimer, the term of this patent is extended or adjusted under 35 U.S.C. 154(b) by 639 days.

(21) Appl. No.: 12/371,008

(22) Filed: Feb. 13, 2009

(65) Prior Publication Data

US 2009/0210061 A1     Aug. 20, 2009

Related U.S. Application Data

(60) Provisional application No. 61/028,624, filed on Feb. 14, 2008.

(51) Int. Cl.
  *A61F 2/44*     (2006.01)
(52) U.S. Cl. ..................................................... 623/17.16
(58) Field of Classification Search ..... 623/17.15–17.16
  See application file for complete search history.

(56) References Cited

U.S. PATENT DOCUMENTS

| | | | |
|---|---|---|---|
| 6,096,080 A | 8/2000 | Nicholson et al. | |
| 6,241,769 B1 | 6/2001 | Nicholson et al. | |
| 6,245,108 B1 | 6/2001 | Biscup | |
| 6,616,695 B1 * | 9/2003 | Crozet et al. | 623/17.11 |
| 6,648,915 B2 | 11/2003 | Sazy | |
| 6,676,703 B2 | 1/2004 | Biscup | |
| 6,752,832 B2 * | 6/2004 | Neumann | 623/17.15 |
| 6,800,093 B2 | 10/2004 | Nicholson et al. | |
| 7,018,414 B2 | 3/2006 | Brau et al. | |
| 7,166,110 B2 | 1/2007 | Yundt | |
| 7,229,477 B2 | 6/2007 | Biscup | |
| 2002/0169507 A1 | 11/2002 | Malone | |
| 2004/0143330 A1 | 7/2004 | Sazy | |
| 2004/0225360 A1 | 11/2004 | Malone | |
| 2005/0070900 A1 | 3/2005 | Serhan et al. | |
| 2005/0209693 A1 | 9/2005 | Lo et al. | |
| 2005/0245942 A1 | 11/2005 | DiPoto | |
| 2006/0116767 A1 | 6/2006 | Magerl et al. | |
| 2006/0173543 A1 | 8/2006 | Brau et al. | |
| 2006/0212118 A1 | 9/2006 | Abernathie | |
| 2006/0241621 A1 * | 10/2006 | Moskowitz et al. | 606/72 |
| 2006/0287725 A1 | 12/2006 | Miller | |
| 2007/0043442 A1 | 2/2007 | Abernathie et al. | |
| 2007/0067035 A1 | 3/2007 | Falahee | |

(Continued)

OTHER PUBLICATIONS

Cayenne medical, "Aperfix System Removal Technique Guide", pp. 1-8.*

*Primary Examiner* — Christopher D Koharski
*Assistant Examiner* — Rebecca Straszheim
(74) *Attorney, Agent, or Firm* — Philips Ryther & Winchester; Matthew D. Thayne (57) ABSTRACT

The disclosure relates to a cage device for performing spinal fusion, including, in some embodiments: a housing defining one or more ports that is selectively disposed in an intervertebral space between adjacent vertebrae; one or more extensible retention structures that are selectively advanced out of the housing through the one or more ports and into one or more endplates of the adjacent vertebrae; and one or more actuation mechanisms for selectively advancing the one or more extensible retention structures out of the housing through the one or more ports and into the one or more endplates of the adjacent vertebrae.

21 Claims, 7 Drawing Sheets

U.S. PATENT DOCUMENTS

| | | |
|---|---|---|
| 2007/0083265 A1 | 4/2007 | Malone |
| 2007/0129804 A1 | 6/2007 | Bentley et al. |
| 2007/0250171 A1* | 10/2007 | Bonin .................. 623/17.15 |
| 2007/0255415 A1* | 11/2007 | Edie et al. .................. 623/17.16 |
| 2007/0276377 A1 | 11/2007 | Yundt |
| 2008/0243254 A1* | 10/2008 | Butler .................. 623/17.16 |

* cited by examiner

ANTERIOR LUMBAR INTERBODY FUSION CAGE DEVICE AND ASSOCIATED METHOD

CROSS-REFERENCE TO RELATED APPLICATION(S)

The present non-provisional patent application claims the benefit of priority of U.S. Provisional Patent Application No. 61/028,624, filed on Feb. 14, 2008, and entitled "ANTERIOR LUMBAR INTERBODY FUSION CAGE DEVICE," the contents of which are incorporated in full by reference herein.

FIELD OF THE INVENTION

The present invention relates generally to devices and methods for performing spinal surgery. More specifically, the present invention relates to an anterior lumbar interbody fusion (ALIF) cage device and an associated method for performing fusion procedures of the lumbar spine. The fundamental concepts underlying this device and method may be extended to other surgical procedures as well, such as extreme lateral interbody fusion (XLIF) spinal procedures, cervical spinal procedures, and the like.

BACKGROUND OF THE INVENTION

ALIF is a spinal fusion procedure that utilizes an anterior (i.e. frontal) approach through the abdominal region to fuse adjacent vertebrae of the lumbar spine. The intervertebral disc is removed using appropriate rasping and grasping tools and replaced with a cage device and/or bone graft after appropriate distraction and spacing tools are used to restore the normal height of the intervertebral space. ALIF is preferred when either one or multiple spinal levels are being fused and one or multiple intervertebral discs must be removed, and may be performed in conjunction with a posterior decompression (i.e. laminectomy) and/or the placement of stabilizing instrumentation (i.e. screws and rods, plates, etc.). Because during ALIF the spinal nerves and other neurologic structures do not have to be retracted, wide access to the intervertebral space(s) of interest is provided without unacceptable risk of neurologic injury. ALIF is used to treat a variety of painful spinal conditions, such as spondylolisthesis and degenerative disc disease, among others.

Conventional ALIF cage devices typically include some sort of retention mechanism to hold them securely in the intervertebral space. Such retention mechanisms include biting and locking structures that engage the endplate(s) of the vertebral body or bodies of interest, screw assemblies that engage the vertebral body or bodies of interest, plate structures that engage the vertebral body or bodies of interest, etc. All of these retention mechanisms, however, suffer from the shortcomings that they are difficult to place, difficult to deploy, and/or tend to allow the associated cage device and/or bone graft to shift over time and thus fail to adequately maintain the normal height of the intervertebral space, for example. Thus, what is needed in the art is an improved ALIF cage device having an improved retention mechanism.

BRIEF SUMMARY OF THE INVENTION

In various exemplary embodiments, the present invention provides an improved ALIF cage device that has one or more extensible threaded retention pipe structures that are selectively deployed into one or more endplates of adjacent vertebrae once the ALIF cage device is disposed in an intervertebral space of interest. A bone graft is disposed within a housing and the extensible threaded retention pipe structure(s) of the ALIF cage device, as appropriate. Advantageously, the extensible threaded retention pipe structure(s) are selectively deployed into the endplate(s) of the adjacent vertebrae via the actuation of a simple keyed screw and gear mechanism or the like. Again, the fundamental concepts underlying the ALIF cage device of the present invention may be extended to other surgical procedures as well, such as XLIF spinal procedures, cervical spinal procedures, and the like.

In one exemplary embodiment, the present invention provides a cage device for performing spinal fusion, including: a housing defining one or more ports that is selectively disposed in an intervertebral space between adjacent vertebrae; one or more extensible retention structures that are selectively advanced out of the housing through the one or more ports and into one or more endplates of the adjacent vertebrae; and one or more actuation mechanisms for selectively advancing the one or more extensible retention structures out of the housing through the one or more ports and into the one or more endplates of the adjacent vertebrae. The housing is sized and shaped to cover substantially all of the one or more endplates of the adjacent vertebrae. Optionally, the housing is at least partially manufactured from a radiolucent material. Preferably, the one or more extensible retention structures each consist of an annular structure having a substantially constant cross-sectional shape. The one or more extensible retention structures each include a cutting edge for engaging bony material of an associated endplate of an adjacent vertebrae. The one or more extensible retention structures each also include internal bone threading for engaging bony material of an associated endplate of an adjacent vertebrae. The one or more extensible retention structures each further include external machine threading for engaging corresponding internal machine threading of the housing and selectively advancing the one or more extensible retention structures out of the housing through the one or more ports and into the one or more endplates of the adjacent vertebrae. Preferably, the machine threading is allowed to escape the housing. The machine threading that is allowed to escape the housing serves to compress an associated endplate of an adjacent vertebrae against the housing. In one exemplary embodiment, the one or more actuation mechanisms consist of at least one worm gear/mandrel pair configured to engage the machine threading. Optionally, the one or more actuation mechanisms consist of at least one worm gear/mandrel pair configured to engage longitudinally oriented teeth manufactured into the machine threading. Preferably, the one or more extensible retention structures each include a retention structure configured to prevent that extensible retention structure from escaping the housing. Thus, the one or more extensible retention structures are selectively advanced out of the housing through the one or more ports and into the one or more endplates of the adjacent vertebrae with a rotational motion. Preferably, the one or more extensible retention structures are configured such that they may contain a bone graft. In one exemplary embodiment, the housing is selectively disposed in the intervertebral space between the adjacent vertebrae using an anterior surgical approach.

In another exemplary embodiment, the present invention provides a method for performing spinal fusion using a cage device, including: providing a housing defining one or more ports that is selectively disposed in an intervertebral space between adjacent vertebrae; providing one or more extensible retention structures that are selectively advanced out of the housing through the one or more ports and into one or more endplates of the adjacent vertebrae; and providing one or more actuation mechanisms for selectively advancing the one or more extensible retention structures out of the housing through the one or more ports and into the one or more endplates of the adjacent vertebrae. The housing is sized and shaped to cover substantially all of the one or more endplates of the adjacent vertebrae. Optionally, the housing is at least partially manufactured from a radiolucent material. Preferably, the one or more extensible retention structures each consist of an annular structure having a substantially constant cross-sectional shape. The one or more extensible retention structures each include a cutting edge for engaging bony material of an associated endplate of an adjacent vertebrae. The one or more extensible retention structures each also include internal bone threading for engaging bony material of an associated endplate of an adjacent vertebrae. The one or more extensible retention structures each further include external machine threading for engaging corresponding internal machine threading of the housing and selectively advancing the one or more extensible retention structures out of the housing through the one or more ports and into the one or more endplates of the adjacent vertebrae. Preferably, the machine threading is allowed to escape the housing. The machine threading that is allowed to escape the housing serves to compress an associated endplate of an adjacent vertebrae against the housing. In one exemplary embodiment, the one or more actuation mechanisms consist of at least one worm gear/mandrel pair configured to engage the machine threading. Optionally, the one or more actuation mechanisms consist of at least one worm gear/mandrel pair configured to engage longitudinally oriented teeth manufactured into the machine threading. Preferably, the one or more extensible retention structures each include a retention structure configured to prevent that extensible retention structure from escaping the housing. Thus, the one or more extensible retention structures are selectively advanced out of the housing through the one or more ports and into the one or more endplates of the adjacent vertebrae with a rotational motion. Preferably, the one or more extensible retention structures are configured such that they may contain a bone graft. In one exemplary embodiment, the housing is selectively disposed in the intervertebral space between the adjacent vertebrae using an anterior surgical approach.

BRIEF DESCRIPTION OF THE DRAWINGS

The present invention is illustrated and described herein with reference to the various drawings, in which like reference numbers are used to denote like device components/method steps, as appropriate, and in which.

DETAILED DESCRIPTION OF THE INVENTION

Figure 1:
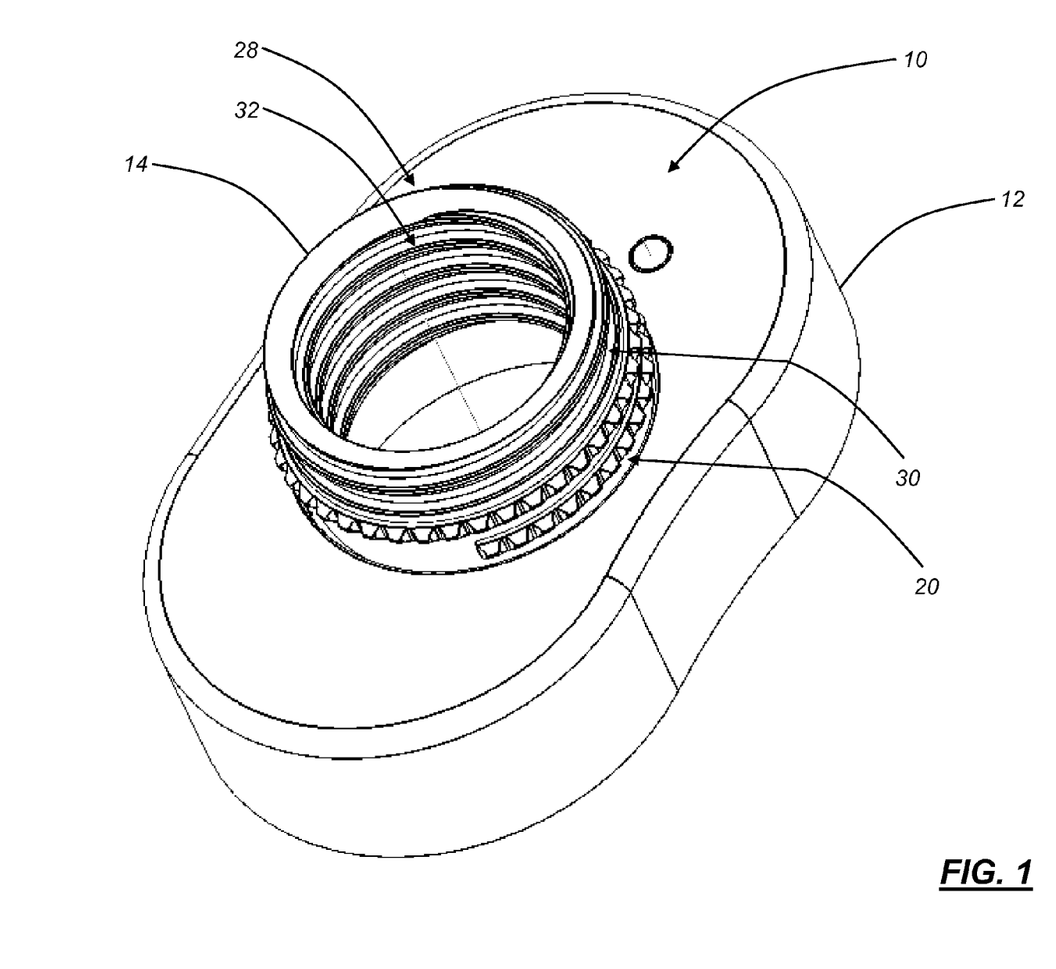
FIG. 1 is a top perspective view of one exemplary embodiment of the top half of the ALIF cage device of the present invention, highlighting the associated housing and extensible threaded retention pipe structure.

Referring to FIG. 1, in one exemplary embodiment, the ALIF cage device 10 of the present invention includes a housing 12 and one or more extensible threaded retention pipe structures 14 that are selectively deployed into one or more endplates of adjacent vertebrae once the ALIF cage device 10 is disposed in an intervertebral space of interest. It should be noted that only the top half of the ALIF cage device 10 is illustrated herein (i.e. the top half of the housing 12 and the top extensible threaded retention pipe structure 14). The bottom half of the ALIF cage device 10 is substantially identical, including the bottom half of the housing 12 and the bottom extensible threaded retention pipe structure 14, when used. The top and bottom halves of the ALIF cage device 10 (i.e. the top and bottom halves of the housing 12) are joined during the manufacturing process or prior to implantation to form an integrated whole. A bone graft is disposed within the housing 12 and the extensible threaded retention pipe structure(s) 14 of the ALIF cage device 10, as appropriate.

Once the ALIF cage device 10 is disposed in the intervertebral space of interest, the extensible threaded retention pipe structure(s) 14 are selectively deployed into the endplate(s) of the adjacent vertebra(e) by deflecting outwards with respect to the housing 12, optionally accompanied by a rotational motion. This deflection outwards is along the cranial/caudal axis of the spine.

Figure 2:
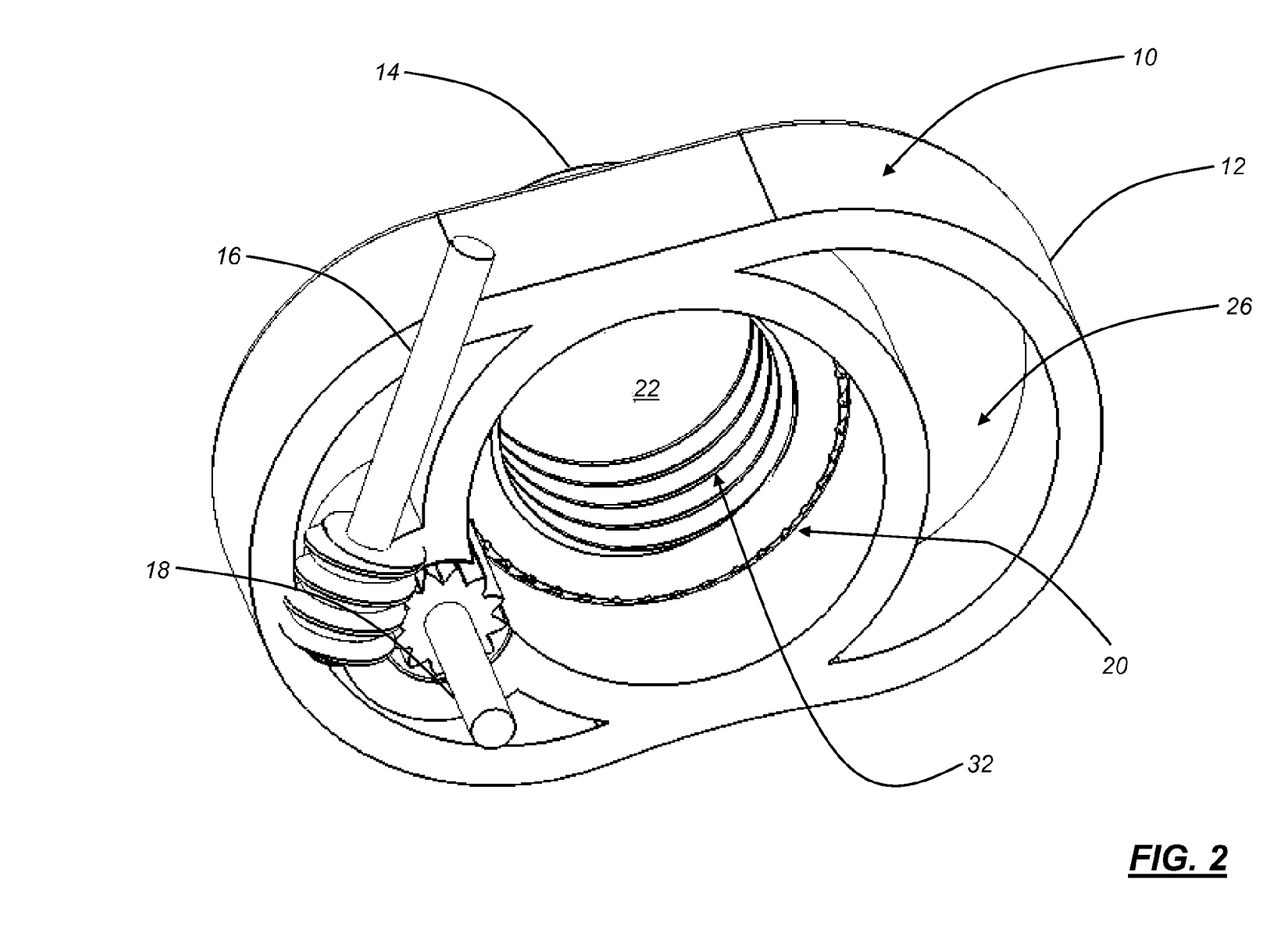
FIG. 2 is a bottom perspective view of the top half of the ALIF cage device of FIG. 1, highlighting the associated housing, extensible threaded retention pipe structure, worm gear, and mandrel.

Referring to FIG. 2, in this exemplary embodiment, the extensible threaded retention pipe structure(s) 14 are each deployed into the endplate(s) of the adjacent vertebra(e) by a worm gear/mandrel pair 16,18. The worm gear 16 is disposed along the anterior/posterior or lateral axis of the ALIF cage device 10, while the mandrel 18 is disposed along the cranial/caudal axis of the ALIF cage device 10. The worm gear 16 disposed along the anterior/posterior or lateral axis of the ALIF cage device 10 has a portion that protrudes or is accessible through a port (not specifically illustrated) manufactured into the associated half of the housing 12. The mandrel 18 disposed along the cranial/caudal axis of the ALIF cage device 10 has portions that are seated in both the top and bottom halves of the housing 12. Thus, the worm gear 16 rotates about the anterior/posterior or lateral axis of the ALIF cage device 10, engages and rotates the mandrel 18, which rotates about the cranial/caudal axis of the ALIF cage device 10 and engages drive threads 20 disposed concentrically about the outside diameter of the associated extensible threaded retention pipe structure 14. Specifically, the mandrel 18 engages longitudinal teeth manufactured into the drive threads 20 disposed concentrically about the outside diameter of the associated extensible threaded retention pipe structure 14. Thus, as the worm gear 16 is actuated by a surgeon and turns the mandrel 18, the extensible threaded retention pipe structure 14 is "spun up" or "spun down" via the longitudinal teeth of these drive threads 20, which engage a complimentary thread manufactured into the interior of the housing 12, or, alternatively, a lip 24 (FIGS. 3 and 4) manufactured into the interior/surface of the housing 12. Preferably, each of the one or more extensible threaded retention pipe structures 14 is capable of extending a distance on the order of millimeters to centimeters from the housing 12 and into the endplate(s) of the adjacent vertebra(e). It will be readily apparent to those of ordinary skill in the art that different mechanisms could also be used to deploy the one or more extensible threaded retention pipe structures 14, using gears and threads or not, employing rotational as well as extension motion or not, etc. For example, one set of worm gears/mandrels 16,18 could be used to deploy both top and bottom extensible threaded retention pipe structures 14 simultaneously. Likewise, different actuation mechanisms and tools could be used for deployment.

Figure 3:
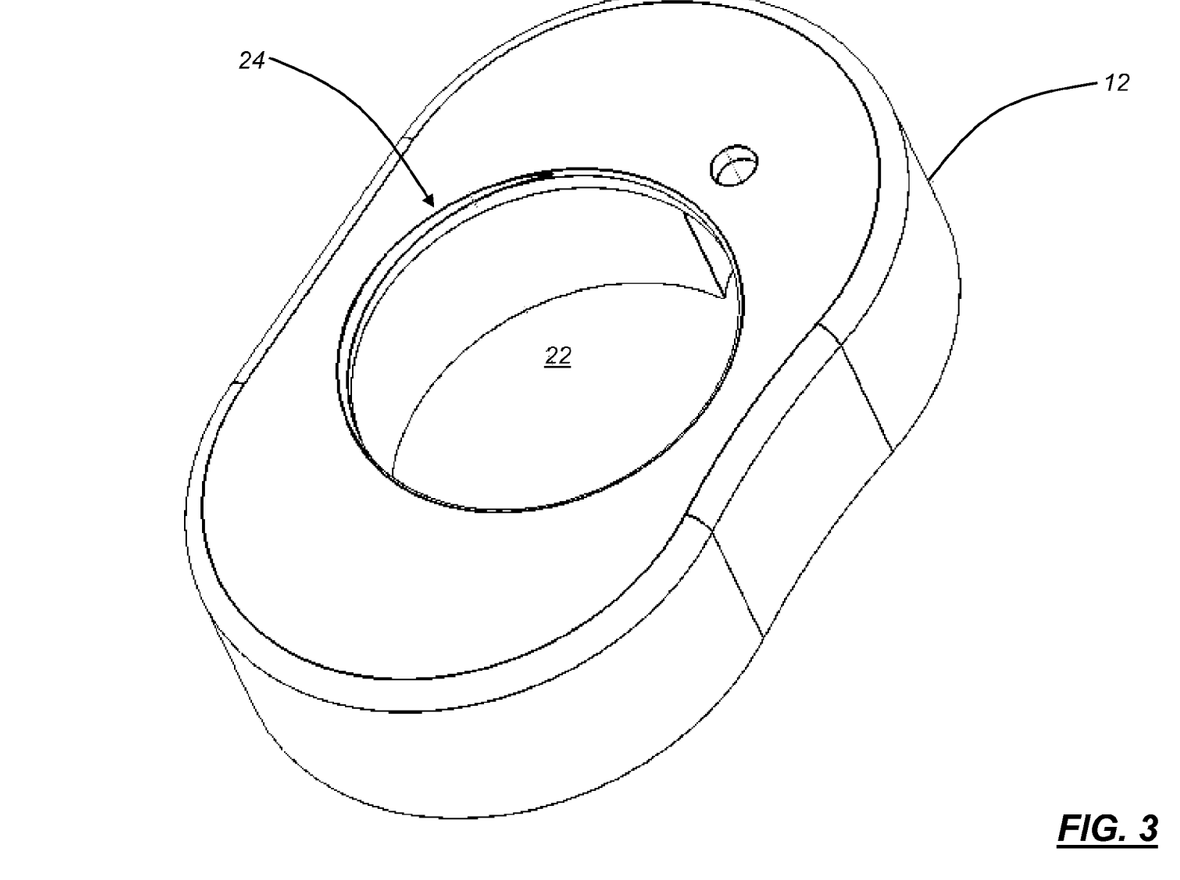
FIG. 3 is a top perspective view of one exemplary embodiment of the housing of FIGS. 1 and 2.

Referring to FIG. 3, in one exemplary embodiment, each half of the housing 12 is sized and shaped such that, collectively, the housing 12 fits comfortably within the intervertebral space into which it is inserted. In the exemplary embodiment illustrated, the housing 12 is substantially oval or "kidney"-shaped, mimicking the shape of the vertebral endplates adjacent to which it is disposed. It is desirable that the ALIF cage device 10 (FIGS. 1 and 2) cover as much of the vertebral endplates as possible. Each half of the housing includes a port 22 through which the associated extensible threaded retention pipe structure 14 (FIGS. 1, 2, 5, and 6) is deployed. As described above, this port 22 may include a thread (not specifically illustrated) manufactured into its interior, or, alternatively, a lip 24 manufactured into its interior, for engaging the longitudinal teeth of the drive threads 20 (FIGS. 1, 2, 5, and 6) of the associated extensible threaded retention pipe structure 14. Preferably, each half of the housing 12 is manufactured from a metal or another biocompatible material, and some or all components of the housing 12 may be manufactured from a radiolucent material that is transparent to X-ray, CT, and MRI imaging modalities, such that anatomical structures may be visualized without interference. As alluded to above, a one-piece housing may be substituted for the two-piece housing illustrated and described without departing from the spirit and scope of the present invention.

Figure 4:
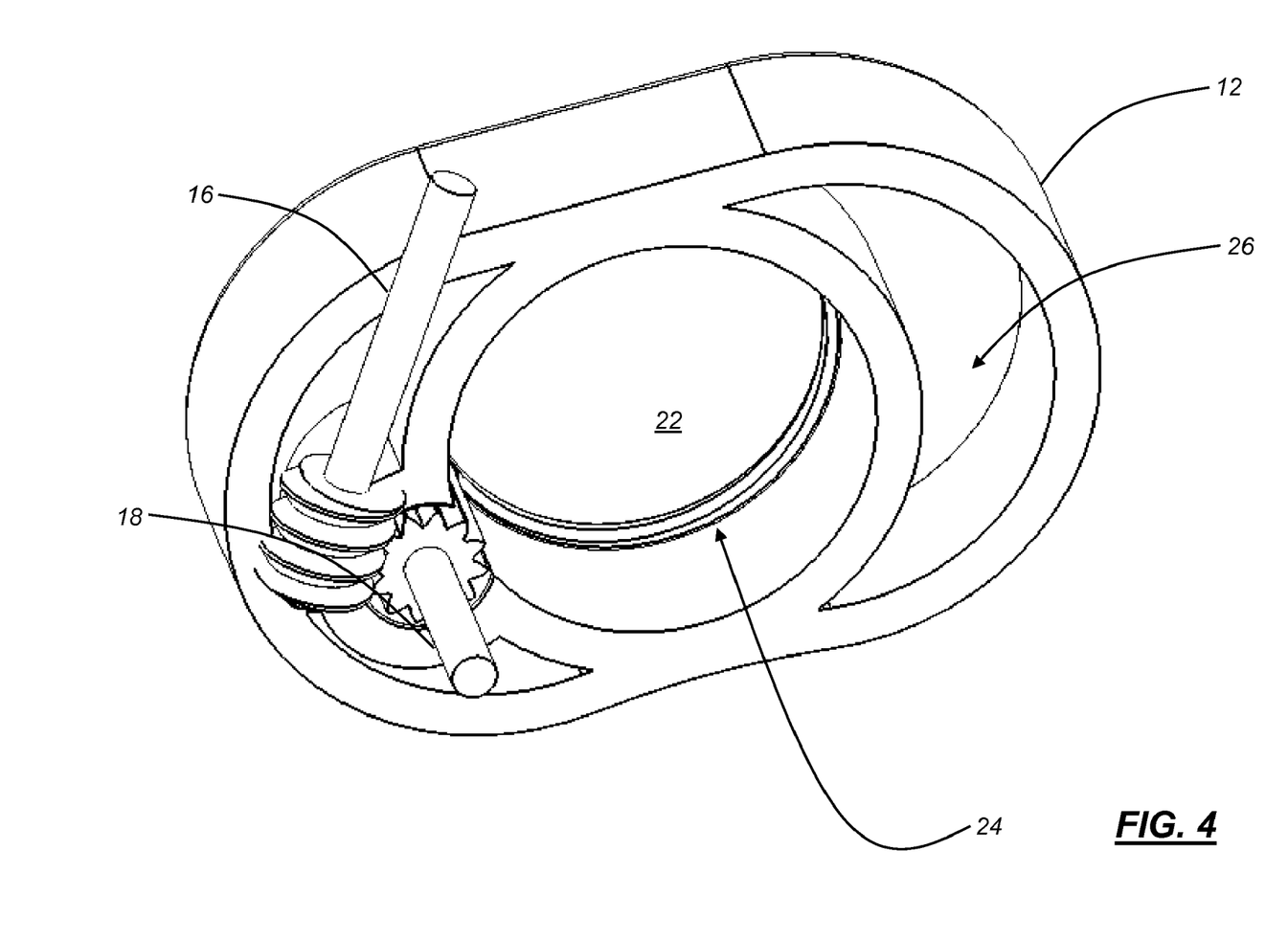
FIG. 4 is a bottom perspective view of the housing of FIG. 3, highlighting the associated worm gear and mandrel.

Referring to FIG. 4, in this exemplary embodiment, each half of the housing 12 includes a substantially hollow interior portion 26, to conserve weight, defining channels or access spaces for the worm gears/mandrels 16,18 and other structures/devices disposed within the housing 12.

Figure 5:
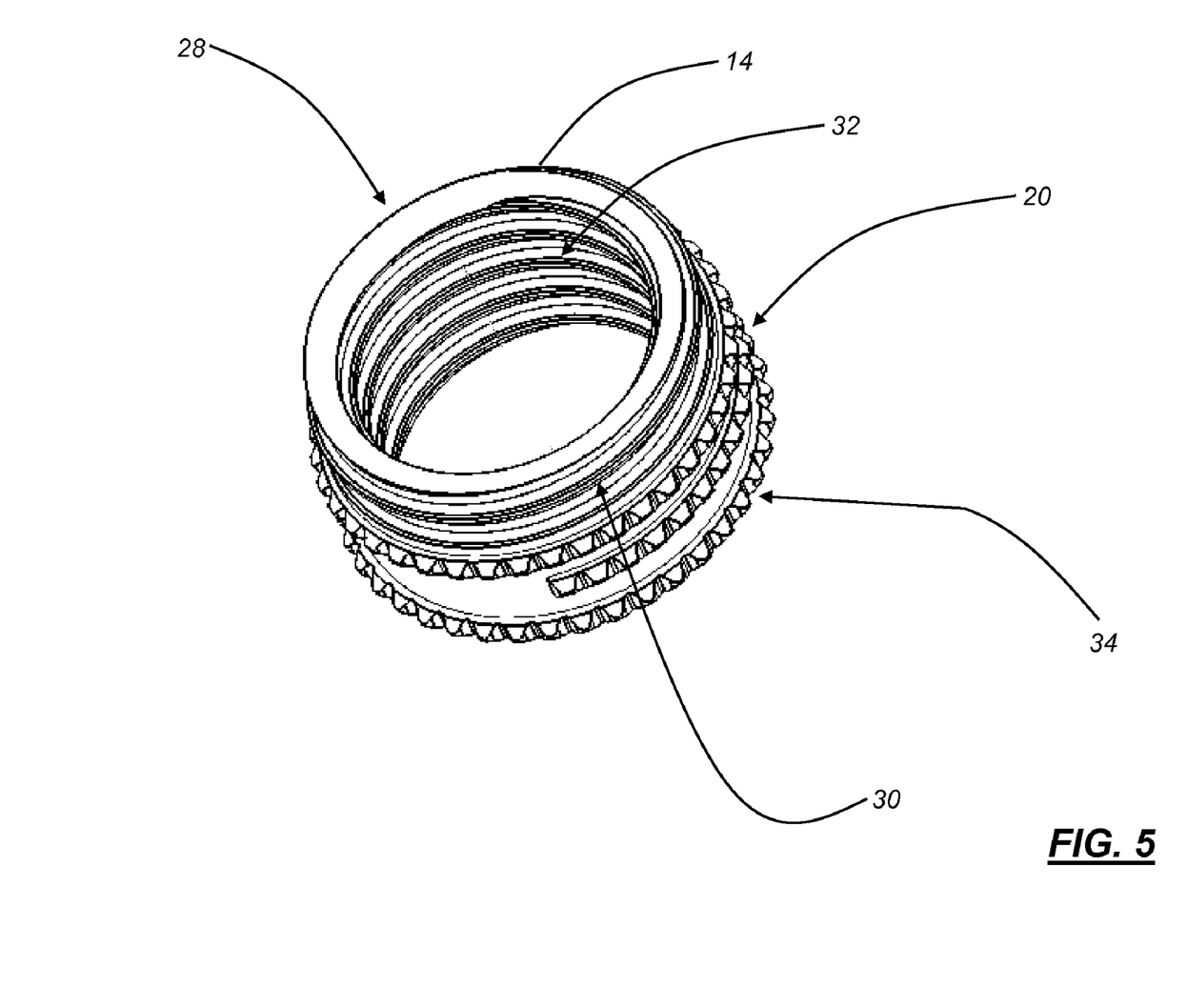
FIG. 5 is a top perspective view of one exemplary embodiment of the extensible threaded retention pipe structure of FIGS. 1 and 2.
Figure 6:
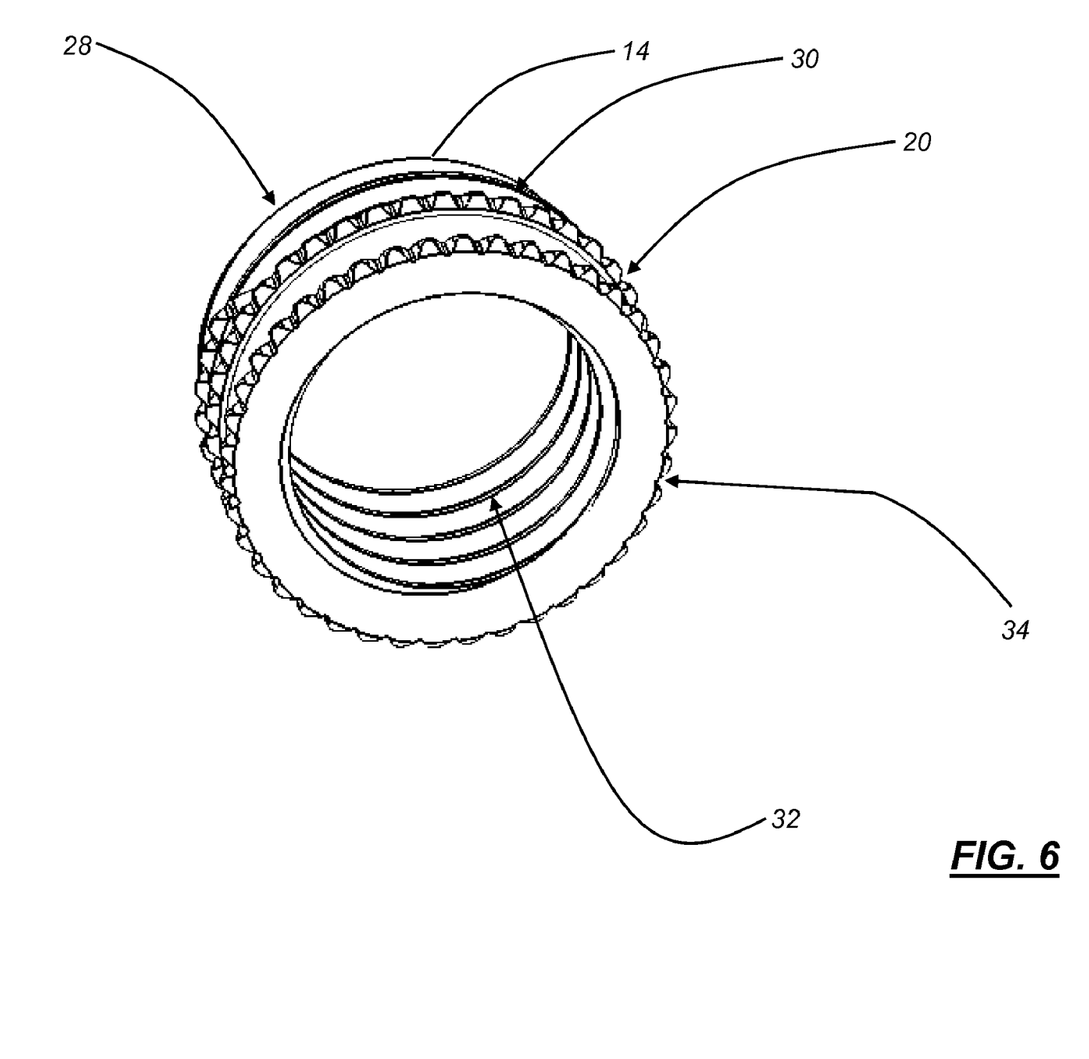
FIG. 6 is a bottom perspective view of the extensible threaded retention pipe structure of FIG. 5.

Referring to FIGS. 5 and 6, in one exemplary embodiment, each extensible threaded retention pipe structure 14 is an annular structure with a substantially circular cross-sectional shape. However, any suitable cross-sectional shape, being constant or variable along the longitudinal axis of the extensible threaded retention pipe structure 14, may be used. Likewise, each extensible threaded retention pipe structure 14 may be a substantially solid structure. Each extensible threaded retention pipe structure 14 is manufactured from a metal or another biocompatible material. Preferably, each extensible threaded retention pipe structure 14 includes a cutting edge 28 along the surface or edge that engages the associated vertebral endplate, such that the extensible threaded retention pipe structure 14 securely seats itself in this bony structure upon deployment. The extensible threaded retention pipe structure 14 also includes threads 30,32 disposed concentrically about its outside and/or inside diameter(s) for this purpose. The outer threads 30 cover about one-half the length of the extensible threaded retention pipe structure 14 and are preferably machine threads, while the inner threads 32 cover substantially the entire length of the extensible threaded retention pipe structure 14 and are preferably bone threads. Finally, each extensible threaded retention pipe structure 14 includes a retention thread or lip 34 configured to engage the lip 24 (FIGS. 3 and 4) manufactured into the interior/surface of the housing 12 (FIGS. 1-4), such that the extensible threaded retention pipe structure 14 cannot be expelled from the housing 12 when "spun up" or "spun down." Preferably, the machine threads 30 stop at least a full turn before the retention thread or lip 34, such that they may "escape" the housing. These machine threads 30 are wider than the retention thread or lip 34. The machine threads 30 may or may not be integral with the drive threads 20 (FIGS. 1, 2, 5, and 6) described above. The pitch of the drive threads 20/machine threads 30 determine the rate at which the extensible threaded retention pipe structure 14 advances out of the housing 12. Once the machine threads 30 are clear of the housing 12, they serve to compress the vertebral endplate(s) against the housing 12.

Again, a bone graft is disposed within the housing 12 and the extensible threaded retention pipe structure(s) 14 of the ALIF cage device 10 (FIGS. 1 and 2), as appropriate. Optionally, the bone graft is accessible through an anterior window (not specifically illustrated) of the ALIF cage device 10 when positioned and seated. This anterior window may be capped at will.

Figure 7:
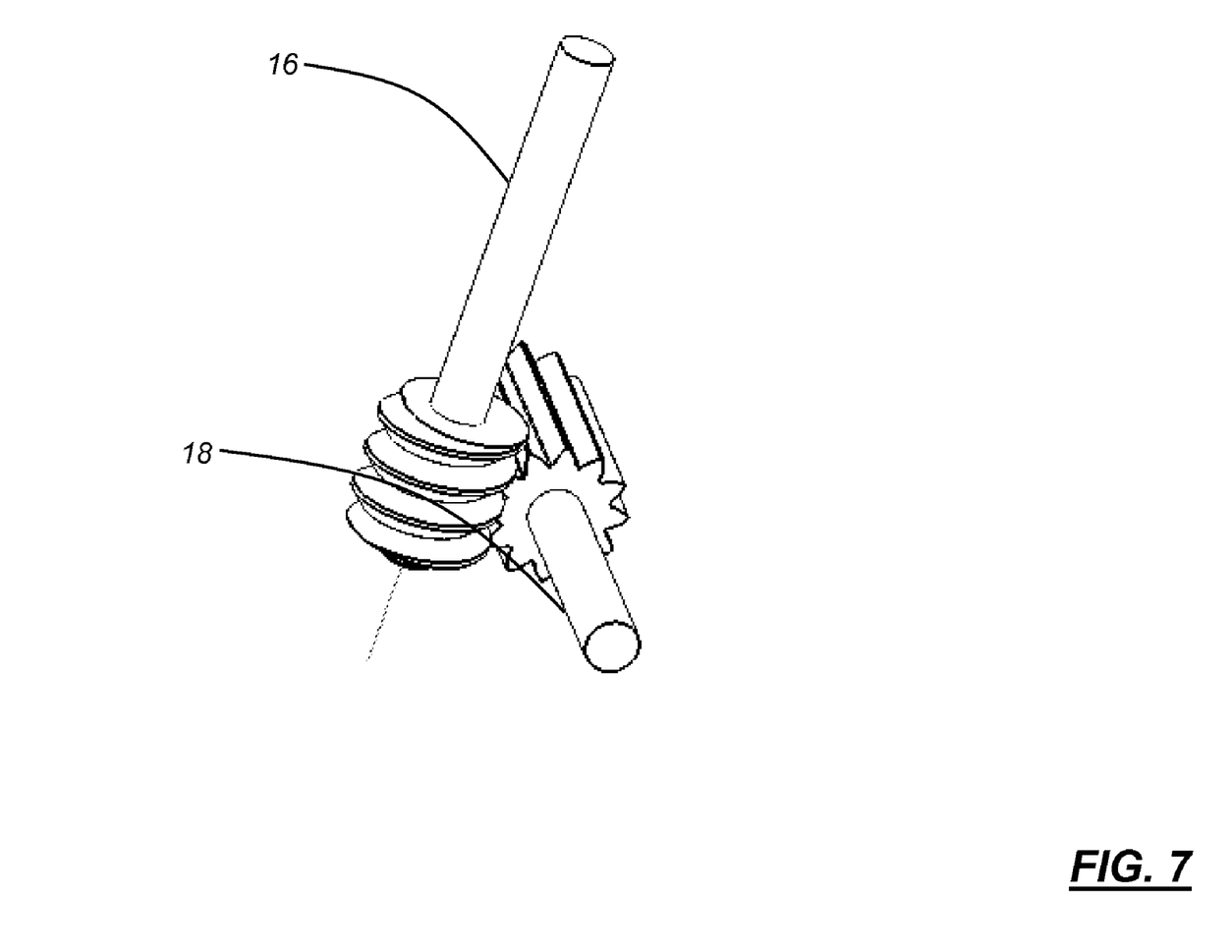
FIG. 7 is a bottom perspective view of one exemplary embodiment of the worm gear and mandrel of FIG. 2.

FIG. 7 is an isolation view of the worm gears/mandrels 16,18 of the exemplary embodiment provided above. Each of these worm gears/mandrels 16,18 is manufactured from a metal or another biocompatible material. Again, it will be readily apparent to those of ordinary skill in the art that different mechanisms could also be used to deploy the one or more extensible threaded retention pipe structures 14 (FIGS. 1, 2, 5, and 6), using gears and threads or not, employing rotational as well as extension motion or not, etc. For example, one set of worm gears/mandrels 16,18 could be used to deploy both top and bottom extensible threaded retention pipe structures 14 simultaneously. Likewise, different actuation mechanisms and tools could be used for deployment.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A cage device for performing spinal fusion, comprising:
a housing defining one or more ports that is configured to be selectively disposed in an intervertebral space between adjacent vertebrae;
one or more extensible retention structures that are configured to be selectively advanced out of the housing through the one or more ports and into one or more endplates of the adjacent vertebrae, wherein the one or more extensible retention structures each comprise external threading and internal threading, wherein the external threading is configured for engaging corresponding internal threading of the housing and selectively advancing the one or more extensible retention structures out of the housing through the one or more ports and into the one or more endplates of the adjacent vertebrae; and
one or more actuation mechanisms configured for selectively advancing the one or more extensible retention structures out of the housing through the one or more ports and into the one or more endplates of the adjacent vertebrae, wherein the one or more actuation mechanisms comprise at least one worm gear/mandrel pair, and wherein the at least one worm gear/mandrel pair is configured to engage longitudinally oriented teeth manufactured into the external threading.

2. The cage device of claim 1, wherein the housing is sized and shaped to cover substantially all of the one or more endplates of the adjacent vertebrae.

3. The cage device of claim 1, wherein the housing is at least partially manufactured from a radiolucent material.

4. The cage device of claim 1, wherein the one or more extensible retention structures each comprise an annular structure having a substantially constant cross-sectional shape.

5. The cage device of claim 1, wherein the one or more extensible retention structures each comprise a cutting edge for engaging bony material of the one or more endplates of the adjacent vertebrae.

6. The cage device of claim 1, wherein the internal threading of the one or more extensible retention structures is configured for engaging bony material of an associated endplate of an adjacent vertebrae.

7. The cage device of claim 1, wherein the one or more extensible retention structures each comprise a retention structure configured to prevent that extensible retention structure from escaping the housing.

8. The cage device of claim 1, wherein the one or more extensible retention structures are selectively advanced out of the housing through the one or more ports and into the one or more endplates of the adjacent vertebrae with a rotational motion.

9. The cage device of claim 1, wherein the one or more extensible retention structures are configured such that they may contain a bone graft.

10. The cage device of claim 1, wherein the housing is configured to be selectively disposed in the intervertebral space between the adjacent vertebrae using an anterior surgical approach.

11. The cage device of claim 1, wherein the external threading comprises drive threads.

12. The cage device of claim 11, wherein the drive threads comprise teeth that are configured for facilitating rotation of at least one of the one or more extensible retention structure to advance at least one of the one or more the extensible retention structures out of the housing through the one or more ports and into one or more endplates of the adjacent vertebrae.

13. A method for performing spinal fusion using a cage device, comprising:
providing a housing defining one or more ports that is selectively disposed in an intervertebral space between adjacent vertebrae;
advancing one or more extensible retention structures out of the housing through the one or more ports such that a cutting edge of the one or more extensible retention structures extends into one or more endplates of the adjacent vertebrae while at least one of the retention structures is rotated, wherein the one or more extensible one or more extensible retention structures are advanced out of the housing by one or more actuation mechanisms, wherein the one or more extensible retention structures each comprise a first threading for engaging corresponding second threading of the housing and selectively advancing the one or more extensible retention structures out of the housing through the one or more ports and into the one or more endplates of the adjacent vertebrae, and wherein the one or more actuation mechanisms comprise at least one worm gear/mandrel pair configured to engage longitudinally oriented teeth manufactured into the first threading.

14. The method of claim 13, wherein the housing is sized and shaped to cover substantially all of the one or more endplates of the adjacent vertebrae.

15. The method of claim 13, wherein the housing is at least partially manufactured from a radiolucent material.

16. The method of claim 13, wherein the one or more extensible retention structures each comprise an annular structure having a substantially constant cross-sectional shape.

17. The method of claim 13, wherein the one or more extensible retention structures each comprise internal bone threading for engaging bony material of the one or more endplates of the adjacent vertebrae.

18. The method of claim 13, wherein the one or more extensible retention structures each comprise a retention structure configured to prevent that extensible retention structure from escaping the housing.

19. The method of claim 13, wherein the one or more extensible retention structures are selectively advanced out of the housing through the one or more ports and into the one or more endplates of the adjacent vertebrae with a rotational motion.

20. The method of claim 13, wherein the one or more extensible retention structures are configured such that they may contain a bone graft.

21. The method of claim 13, wherein the housing is selectively disposed in the intervertebral space between the adjacent vertebrae using an anterior surgical approach.

* * * * *